United States Patent [19]
Goebel

[11] Patent Number: 5,373,544
[45] Date of Patent: Dec. 13, 1994

[54] X-RAY DIFFRACTOMETER

[75] Inventor: Herbert Goebel, Munich, Germany

[73] Assignee: Siemens Aktiengesellschaft, Munich, Germany

[21] Appl. No.: 80,819

[22] Filed: Jun. 24, 1993

[30] Foreign Application Priority Data

Aug. 12, 1992 [DE] Germany .............................. 4226707

[51] Int. Cl.$^5$ ............................................ G01N 23/207
[52] U.S. Cl. .......................................... 378/71; 378/81; 378/149
[58] Field of Search ..................... 378/71, 73, 75, 79, 378/81, 84, 149

[56] References Cited

U.S. PATENT DOCUMENTS

| | | |
|---|---|---|
| 2,805,342 | 9/1957 | Lang . |
| 4,144,450 | 3/1979 | Goebel . |
| 4,274,000 | 6/1981 | Goebel .............................. 378/81 X |
| 4,910,758 | 3/1990 | Herrick ................................. 378/71 |
| 5,046,077 | 9/1991 | Murayama .......................... 378/81 X |

FOREIGN PATENT DOCUMENTS

| | | |
|---|---|---|
| 0456897 | 11/1991 | European Pat. Off. . |
| 1589405 | 5/1970 | France . |
| 1126767 | 9/1968 | United Kingdom . |
| 2083969 | 3/1982 | United Kingdom . |

OTHER PUBLICATIONS

Patent Abstracts of Japan, vol. 017, No. 399 (P-1579), Jul. 26, 1993.
"Identifizierung kristalliner Phasen und Phasenkinetik von Festkörperreaktionen durch Pulver-Röntgendiffratktometrie," Göbel, Siemens Forsch.-u. Entwickl. Ber., vol. 14, No. 4 (1985) pp. 167–176.

Primary Examiner—David P. Porta
Attorney, Agent, or Firm—Hill, Steadman & Simpson

[57] ABSTRACT

An x-ray diffractometer is equipped with a position sensitive detector and a collimator preceding the detector. The lamellae of the collimator are radially aligned to the specimen, which is arranged in the center of a measurement circle along which the detector and collimator move during a measurement. Therefore, only the x-radiation scattered at the specimen contributes to the measured signal. An elliptically deformed multi-layer mirror is provided at the primary beam side, which deflects the source radiation in the direction of the specimen without great intensity loss and focuses it at a point lying on the measurement circle. Analysis of powdered specimens that are enclosed in glass capillaries can be undertaken. A low-background measurement of diffraction diagrams in an x-ray diffractometer given efficient use of the primary beam is achieved.

10 Claims, 3 Drawing Sheets

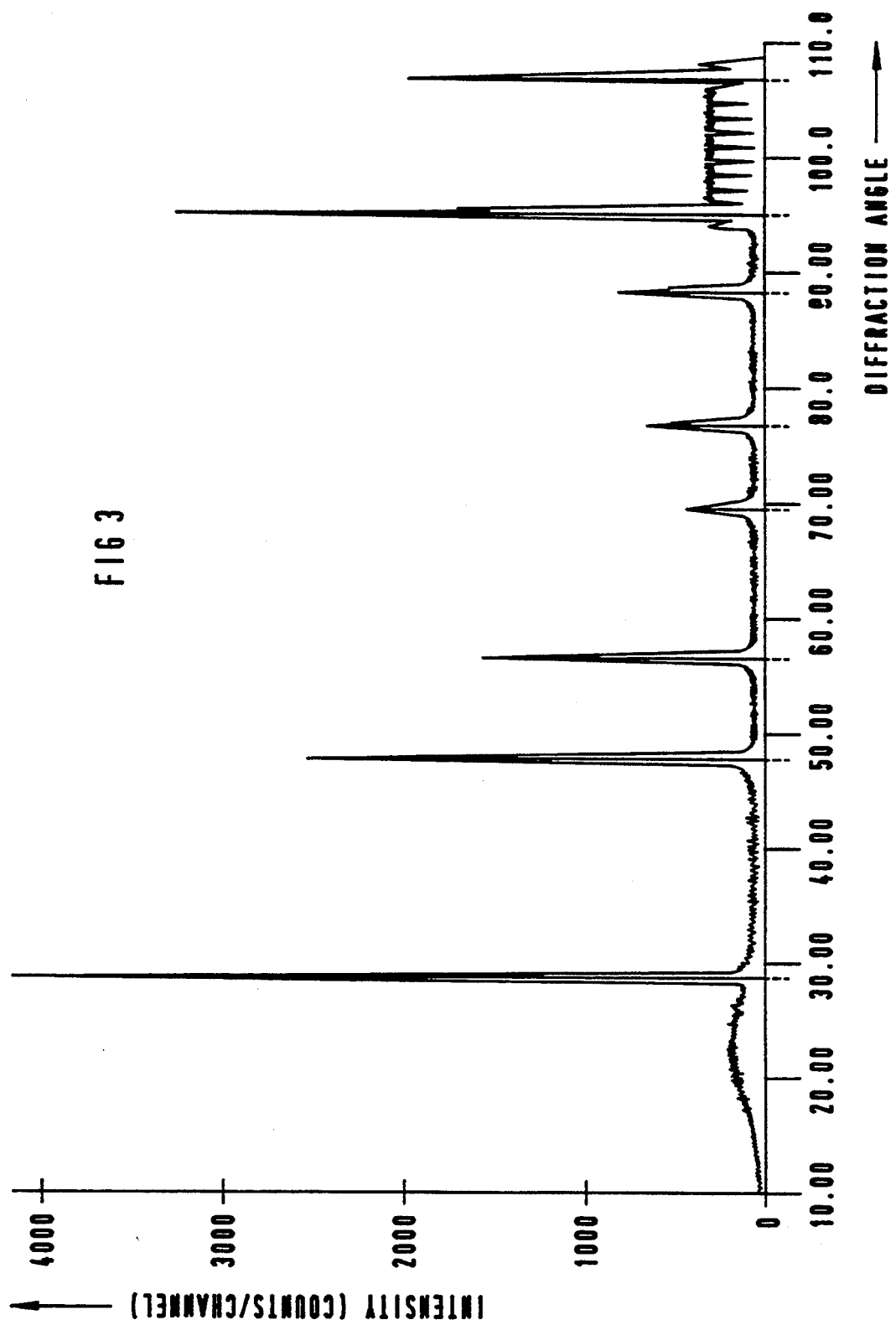

X-RAY DIFFRACTOMETER

BACKGROUND OF THE INVENTION

1. Field of the Invention

The present invention is directed to an x-ray diffractometer for conducting a spectral analysis of a specimen.

2. Description of the Prior Art

X-ray spectrometers serve the purpose of non-destructive analysis of solid, powdered and liquid specimens. Powder x-ray diffractometers have achieved wide usage among devices of this type, because they have a relatively simple structure and are versatilely employable. With such a device, unknown substances and substance mixtures can be identified, their lattice structure can be defined and conclusions about their crystallization state can be made from the diffraction diagrams acquired (see, for example, Siemens Forschungs- und Entwicklungsberichte, Vol. 14 (1985) No. 4, pages 167–176).

Powder diffractometers predominately employ focusing beam arrangements that guarantee a high exploitation of the x-ray beam irradiating the specimen. In order to obtain a beneficial contrast of diffraction maxima relative to background, monochromator crystals are often utilized at the primary side or secondary side. The secondary monochromators are usually composed of bent graphite mosaic crystals and have the advantage that they are capable of separating the usable diffraction radiation from the fluorescent radiation which is unavoidably produced in the specimen.

The mensuration technology of radiography was decisively enriched in the 1980's by the employment of position sensitive detectors. These detectors act as a plurality of individual counters and thus allow significantly faster data collection. As a consequence of the increases in the measuring speed by more than a factor 100 accompanying this, advance "snapshots" of chronologically variable conditions (solid state reactions, phase conversions) are capable of being made in the specimen.

Position sensitive detectors have especially proven useful in combination with monochromators on the primary side. Strictly focusing primary monochromators of high-perfection single crystals (germanium, silicon, quartz) are preferred in such combinations because these crystals are capable of resolving the $K\alpha_1$–$K\alpha_2$ doublets that are problematical for the interpretation of the diffraction diagrams. Diagrams having only $K\alpha_1$ reflexes are therefore obtained, whereby the intensity loss of the primary x-ray caused by the monochromator is more than compensated by the employment of the position sensitive detector.

Compared to conventional methods of x-ray analysis, a technique referred to as total reflection x-ray fluorescence analysis (TXRF) has a high surface sensitivity, since the exciting radiation is incident on the specimen under examination at an extremely small angle $\alpha < 0.5°$, and thus penetrates only a few nanometers into the specimen. The TXRF method is therefore particularly suited for the identification of the chemical composition of thin layers and surfaces. A TXRF measuring apparatus is described in European Application 0 456 897. Instead of having a monochromator of the primary side, this measuring instrument has a multi-layer mirror that deflects the radiation generated in an x-ray tube in the direction toward the specimen under examination without a greater loss in intensity.

SUMMARY OF THE INVENTION

It is an object of the invention is to provide an x-ray diffractometer wherein a low-background measurement of x-ray diffraction diagrams is possible. In particular, it should be guaranteed that only the x-radiation scattered by the specimen under examination proceeds to the detector. A reduction of the background in the diffraction diagrams is particularly desirable in the examination of specimens enclosed in glass capillaries.

The above objects are achieved in accordance with the principles of the present invention in an x-ray diffractometer having a source of x-rays, a focusing reflector which deflects the x-rays in the direction of a specimen, a position sensitive detector which is displaceable along a measurement circle for angle-dependent detection of the x-rays scattered at the specimen, and a collimator preceding the detector having lamellae which are radially aligned onto the specimen, the specimen being disposed at the center of the measurement circle.

The advantage obtainable with the invention is that the detection sensitivity is noticeably improved due to the efficient shielding of the background radiation by the collimator. It is therefore possible without further difficulty to arrange other experimentation devices, particularly a heating furnace, in the immediate proximity of the specimen without degrading the measurement quality.

DESCRIPTION OF THE DRAWINGS

FIG. 3 shows a diffraction diagram registered with the x-ray diffractometer of the invention.

DESCRIPTION OF THE PREFERRED EMBODIMENTS

Figure 1:
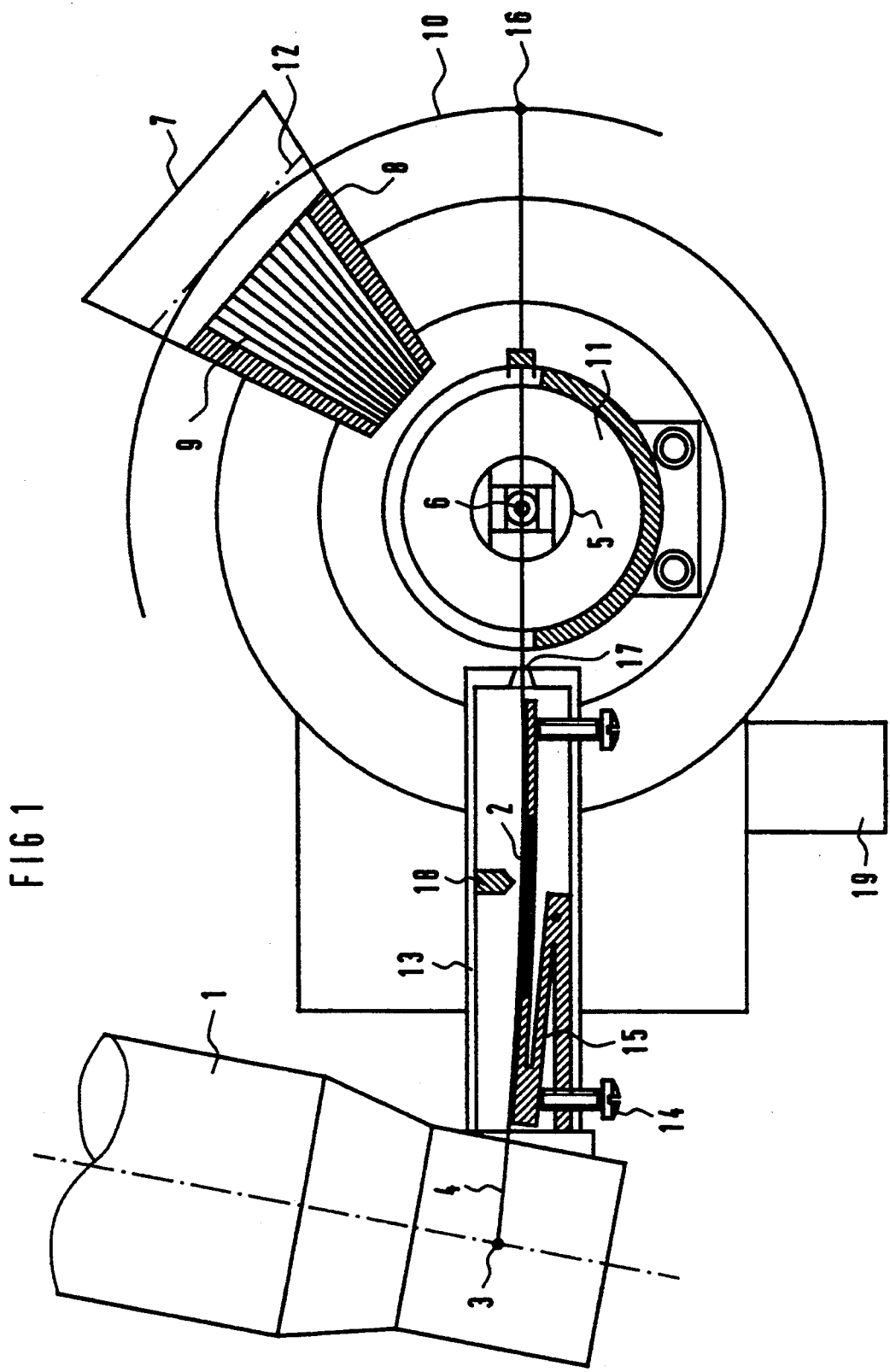
FIG. 1 is a schematic showing of an exemplary embodiment of an x-ray diffractometer constructed in accordance with the principles of the present invention.

As schematically shown in FIG. 1, the x-ray diffractometer of the invention includes an x-ray tube 1 which produces x-radiation 4 generated in a line-shaped electron beam focus 3 on the tube anode. A curved reflector 2 deflects the x-radiation 4 in the direction of the specimen 6 mounted on a conventional goniometer head 5. At least a portion of the scattered radiation thereby produced proceeds to a position sensitive detector 7, having a collimator 8 that precedes the detector 7. Since the lamellae 9 of the collimator 8 are radially aligned to the specimen 6, which is arranged in the center of a measurement circle 10, only the x-radiation scattered at the specimen 6 contributes to the measured signal. Other stray radiation is largely shielded by the collimator 8. It is therefore possible for the first time, for example, to arrange a cylindrical heating furnace 11 in the immediate proximity of the specimen 6 enclosed in a glass capillary (Mark tube) without the stray radiation emanating from the furnace walls and mounts, etc., having a disturbing effect as elevated background in the diffraction diagrams measured at various temperatures.

The position sensitive detector 7 may be a linear proportional counter. This is arranged such that its counter wire 12 tangentially touches the measurement circle 10. As a consequence of its limited expansion, the detector 7 can simultaneously acquire the x-radiation scattered at the specimen 6 only within an angular range of, for example, 10° through 20°. It is therefore necessary for registering the entire diffraction diagram to displace the unit consisting of the detector 7 and the collimator along the measurement circle 10 with a stepping motor 19. Data acquisition thereby preferably ensures by employing the measuring method disclosed in German Patentschrift 26 37 945. It is thereby also assured that no shadowing effects caused by the collimator 8 occur in the diffraction diagram (also see FIG. 3).

As already mentioned, crystal monochromators of the primary side have a low, integral reflectivity. Considerable intensity losses also occur with the employment of a broad band monochromator composed of a combination of reflection and transmission mirrors, since the transmission mirrors are highly absorbent. Additionally, a complicated mechanics is needed in order to align the individual components relative to one another as well as relative to the x-ray source and relative to the specimen. In order to guarantee a better utilization of the intensity of the primary x-ray beam 4, the x-ray diffractometer of the invention employs a multi-layer mirror 2 arranged in a housing 13 as a reflector. This multi-layer mirror has a high reflectivity (reflectivity above 80%) and is elliptically or circularly deformed with the assistance of a bending means composed of a set screw 14 and a lever element 15 such that it focuses the x-radiation 4 deflected in the direction of the specimen 6 in a point 16 lying on the measurement circle 10. The diaphragms 17 and 18 present at or in the housing 13 serve the purpose of limiting the beam cross section in the horizontal and vertical directions.

Figure 2:
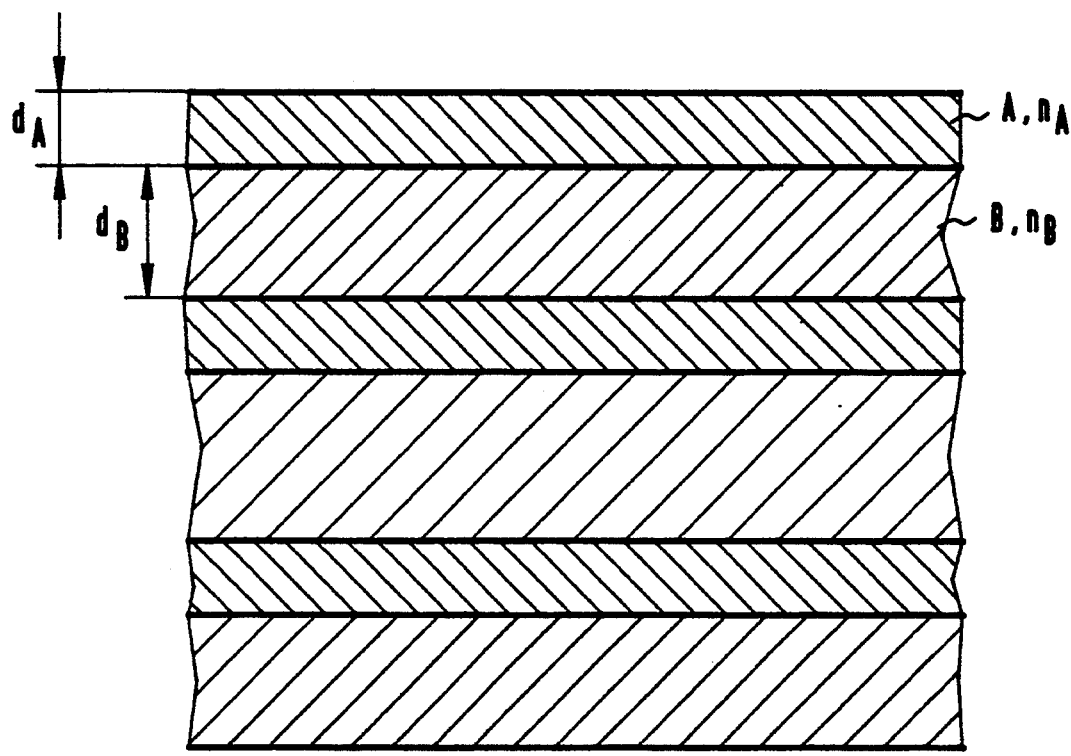
FIG. 2 the schematic structure of the reflector employed in the x-ray diffractometer of FIG. 1.

The multi-layer mirror schematically shown in FIG. 2 is composed of a periodically repeating sequence of layers of materials A and B having different refractive indices $n_A$ and $n_B$, whereby the plurality N of the layers within a period satisfies the condition $N \geq 2$. This layer sequence is preferably produced by sputtering, vapor-deposition or by growing the corresponding materials A or B on a silicon substrate. The layers themselves can be amorphous or crystalline. For example, one of the following combinations of the materials A/B may be used for a mirror composed of a periodic sequence of two layers: Mo/B$_4$C, Re/Si, Re/C, W/Si, W/C, Ta/Si, W/Be, Mo/Be, Mo/Si, Mo/C, Ni/C, Au/C, AuPd/C, ReW/B, ReW/C, Al/Be or V/C. The periodicity length $d=d_A+d_B$ ($d_A$=thickness of the layer A, $d_B$=thickness of layer B), as well as the layer thickness ratio $d_A:d_B$ of layers having a high and low refractive index $n_A$ or $n_B$, are freely prescribable. Therefore, the properties of the reflector 2 can be well-matched to the respective experimental conditions.

The diffraction diagram shown in FIG. 3 was registered with the x-ray diffractometer of the invention using the measurement method disclosed in German Patentschrift 26 37 945. A silicon powder that was charged with Cu-K-Alpha radiation and was enclosed in a 0.5 mm thick quartz capillary served as the specimen (tube parameter: 35 kV/28 mA). The intensity (counting rate per channel, measured in the position sensitive proportional counter 7 is entered dependent on the angle of deflection. Since the detector 7 moved on the measurement circle during the measurement with a speed of 30°/minute, only approximately 3 minutes were required for registering the diffraction diagram in the angular range between 0° and 95°. The angular range between 95° and 110° was registered with a stationary detector. One can clearly see the shadowing effect caused by the collimator 8 that does not appear in the remaining diffraction diagram.

The invention, of course, is not limited to the exemplary embodiment that has been set forth. Thus, it is possible without further difficulty to replace the multi-layer mirror with a total reflection mirror and to correspondingly deform the latter. As in the case of the multi-layer mirror, the deformation can be elliptical, circular or parabolic (focus in the infinite, parallel primary beam). Detectors known as "Curved PSPC" (Curved Position Sensitive Proportional Counter) and other wide-angled detectors, of course, may be used as the position sensitive detector. Further, the specimen need not necessarily be in powdered form. Rod-shaped preparations, planar specimens and single crystals are likewise suitable for investigation in the x-ray diffractometer of the invention.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray diffractometer comprising:
   an x-ray source;
   focusing reflector means for deflecting x-rays from said source in the direction of a specimen;
   position sensitive detector means and means for displacing said detector means along a measurement circle for angle-dependent detection of x-rays scattered at said specimen;
   means for mounting said specimen at the center of said measurement circle; and
   a collimator preceding said detector means having a plurality of lamellae radially aligned onto said specimen at the center of said measurement circle.

2. An x-ray diffractometer as claimed in claim 1 wherein said reflector means is circularly deformed.

3. An x-ray diffractometer as claimed in claim 1 wherein said reflector means is elliptically deformed.

4. An x-ray diffractometer as claimed in claim 1 wherein said reflector means is parabolically deformed.

5. An x-ray diffractometer as claimed in claim 1 wherein said reflector means comprises a total reflection mirror.

6. An x-ray diffractometer as claimed in claim 1 wherein said reflector means comprises a multi-layer mirror.

7. An x-ray diffractometer as claimed in claim 1 wherein said x-ray source produces an x-ray focus lying on said measurement circle.

8. An x-ray diffractometer as claimed in claim 1 wherein said specimen is a powdered specimen, and wherein said means for mounting said specimen includes a capillary enclosing said powdered specimen.

9. An x-ray diffractometer as claimed in claim 1 wherein said position sensitive detector means comprises a linear proportional counter.

10. An x-ray diffractometer as claimed in claim 1 wherein said position sensitive detector comprises a curved proportional counter.

* * * * *